United States Patent
Nishigaki et al.

(10) Patent No.: US 6,489,340 B1
(45) Date of Patent: Dec. 3, 2002

(54) MACROLIDE COMPOUNDS FOR INDUCING CHONDROGENIC DIFFERENTIATION

(75) Inventors: Fusako Nishigaki, Osaka (JP); Susumu Miyata, Hashimoto (JP)

(73) Assignee: Fujisawa Pharmaceutical., Ltd., Osaka (JP)

( * ) Notice: Subject to any disclaimer, the term of this patent is extended or adjusted under 35 U.S.C. 154(b) by 0 days.

(21) Appl. No.: 09/926,700

(22) PCT Filed: May 31, 2000

(86) PCT No.: PCT/JP00/03533
§ 371 (c)(1),
(2), (4) Date: Dec. 4, 2001

(87) PCT Pub. No.: WO00/74665
PCT Pub. Date: Dec. 14, 2000

(30) Foreign Application Priority Data

Jun. 4, 1999 (AU) ............................................. PQ0787

(51) Int. Cl.⁷ .............................................. A61K 31/33
(52) U.S. Cl. ...................... 514/321; 514/410; 514/411; 514/183
(58) Field of Search ................ 514/183, 321, 514/410, 411

(56) References Cited

FOREIGN PATENT DOCUMENTS

WO   99 34836   7/1999

OTHER PUBLICATIONS

Dell, C. P., Current Medicinal Chemistry, 5(3),, 179–194 (1998) (abstract).*
Attur et al., 9th International Congress of Immunology, pp. 858 (1995) (abstract).*
Fukui et al., Ensho, 18(1), 25–30 (1998) (abstract).*

John W. Fuseler et al.: "FK506 attenuates developing and established joint inflammation and suppresses interleukin 6 and nitric oxide expression in bacterial cell wall induced polyarthritis." Journal of Rheumatology, vol. 27, No. 1: pp. 190–199 Jan. 2000.

P.A. Merkel et al.: "Investigational agents for rheumatoid arthritis." Rheumatic Disease Clinics of North America: pp. 779–796 1995.

K. Migita et al.: "The effects of the immunosuppressant rapamycin on the growth of rheumatoid arthritis (RA) synovial fibroblast." Clinical and Experimental Immunology, vol. 104, No. 1: pp. 86–91 1996.

Sa Yocum et al: "Bafilomycin A1 inhibits IL–1–stimulated proteoglycan degradation by chondrocytes without affecting stromelysin synthesis." Archives of Biochemistry and Biophysics: pp. 316 and 827–835 Feb. 01, 1995.

Database Chemabs'Online!Chemical Abstracts Service, Columbus, Ohio, US: Wakako Fukui et al.: "Effect of FK506 on adjuvant arthritis in rats. Studies on the expression of fibroblast growth factor–1 and tyrosine phosphorylated proteins." Retrieved from STN Database accession No. 128:188461 (1998).

* cited by examiner

Primary Examiner—Phyllis G. Spivack
(74) Attorney, Agent, or Firm—Oblon, Spivak, McClelland, Maier & Neustadt, P.C.

(57) ABSTRACT

Chondrogenic differentiations is induced by administering a macrocyclic lactone to mammals to prevent or treat damage to cartilage.

18 Claims, 1 Drawing Sheet

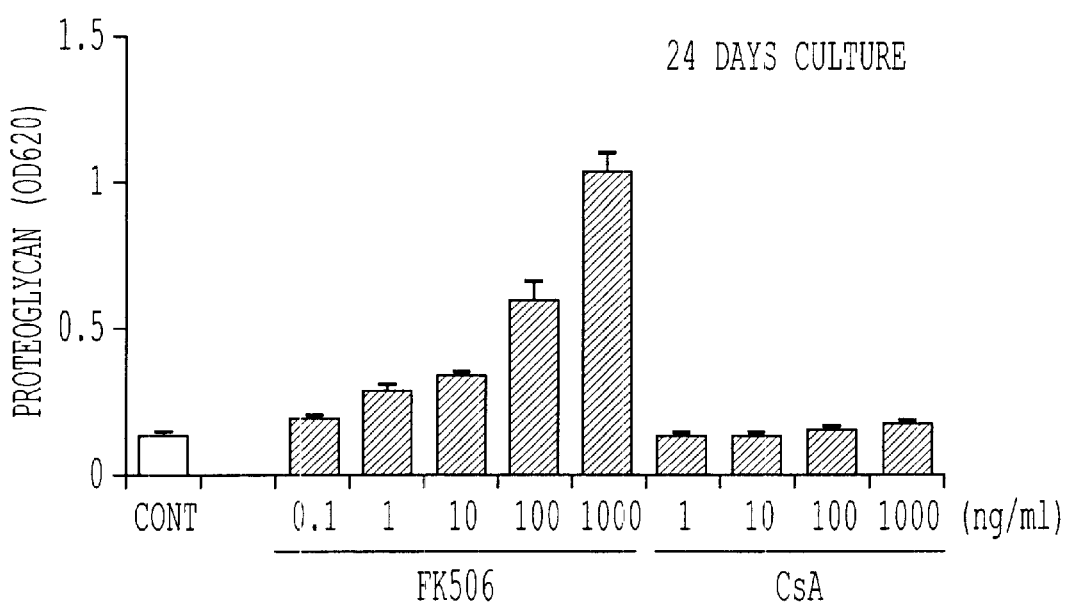

MACROLIDE COMPOUNDS FOR INDUCING CHONDROGENIC DIFFERENTIATION

TECHNICAL FIELD

This invention relates to a new use of macrolide compounds for inducing chondrogenic differentiation.

DISCLOSURE OF INVENTION

The inventors of this invention have surprisingly found that the macrolide compounds mentioned here-in-below has an inducing activity of chondrogenic differentiation.

Accordingly, this invention provides a new use of the macrolide compounds for inducing chondrogenic differentiation.

Further, this invention provides an agent for inducing chondrogenic differentiation, which comprises the macrolide compounds.

Still further, this invention provides a method for inducing chondrogenic differentiation, which comprises administering said macrolide compounds to mammals.

Still further, this invention provides a method for preventing or treating damages of cartilage, which comprises administering said macrolide compounds to mammals.

The term "macrolide compound" for use in accordance with the invention is the generic name of compounds with 12 members or more, which belong to macrocyclic lactones.

As a particular example of the macrolide compound, the tricyclic compound of the following formula (I) can be exemplified.

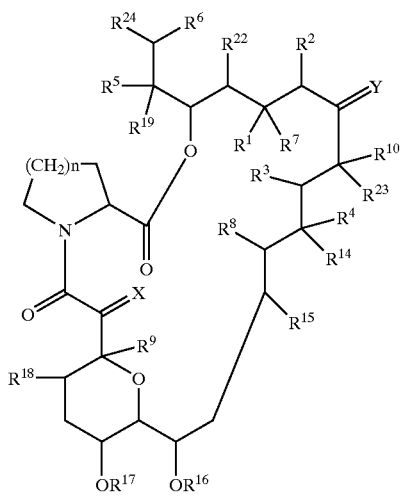

(I)

(wherein each of adjacent pairs of $R^1$ and $R^2$, $R^3$ and $R^4$, and $R^5$ and $R^6$ independently
  (a) are two adjacent hydrogen atoms, and $R^2$ may optionally be an alkyl group, or
  (b) forms another bond formed between the carbon atoms to which they are attached;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, a hydrogen atom and a hydroxy group, (a hydrogen atom and a hydrogen atom), or a group represented by the formula —$CH_2O$—;

Y is an oxo group, (a hydrogen atom and a hydroxy group), (a hydrogen atom and a hydrogen atom), or a group represented by the formula N—$NR^{11}R^{12}$ or N—$OR^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring system which may contain one or more heteroatoms;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —$CH_2Se(C_6H_5)$, and an alkyl substituted by one or more hydroxy groups.

The definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the "protected amino" are 1-(lower alkylthio)-(lower) alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenyl-silyl, etc.), more preferably tri(C1–$C_4$)alkylsilyl group and $C_1$–$C_4$ alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri(lower)alkylsilyl(lower)alkoxycarbonyl(lower)alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include or(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2trifluoromethyl-2-propoxy-2-phenylacetyl, etc.

More preferable acyl groups among the aforesaid acyl groups are $C_1-C_4$ alkanoyl group optionally having carboxy, cyclo $(C_5-C_6)$alkoxy$(C_1-C_4)$alkanoyl group having two $(C_1-C_4)$ alkyls at the cycloalkyl moiety, camphorsulfonyl group, carboxy-$(C_1-C_4)$alkylcarbamoyl group, tri$(C_1-C_4)$alkylsilyl$(C_1-C_4)$alkoxycarbonyl$(C_1-C_4)$alkylcarbamoyl group, benzoyl group optionally having one or two nitro groups, benzenesulfonyl group having halogen, or phenyl $(C_{1-C4})$alkanoyl group having $C_1-C_4$ alkoxy and trihalo $(C_1-C_4)$alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

$R^{24}$ is an optionally substituted ring system which may contain one or more heteroatoms. Preferably $R^{24}$ may be cyclo$(C_{5-7})$alkyl group optionally having suitable substituents, and the following ones can be exemplified.

(a) a 3,4-di-oxo-cyclohexyl group;
(b) a 3-$R^{20}$-4-$R^{21}$-cyclohexyl group,
   in which
   $R^{20}$ is hydroxy, an alkoxy group, an oxo group, or
      a —OCH$_2$OCH$_2$CH$_2$OCH$_3$ group, and
   $R^{21}$ is hydroxy, —OCN, an alkoxy group, a heteroaryloxy which may be substituted by suitable substituents, 1- or 2-tetrazolyl, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—,
   in which
   $R^{25}$ is optionally protected hydroxy or protected amino, and
   $R^{26}$ R is hydrogen or methyl, or
   $R^{20}$ and $R^{21}$ together form an oxygen atom in an epoxide ring; or
(c) cyclopentyl group substituted by methoxymethyl, optionally protected hydroxymethyl, acyloxymethyl
   (in which the acyl moiety optionally contains either a dimethylamino group which may be quaternized, or a carboxy group which may be esterified), one or more amino and/or hydroxy groups which may be protected, or aminooxalyloxymethyl. A preferred example is a 2-formyl-cyclopentyl group.

"A heteroaryl which may be substituted by suitable substituents" moiety of the "heteroaryloxy which may be substituted by suitable substituents" may be the ones exemplified for $R^1$ of the compound of the formula of EP-A-532,088, with preference given to 1-hydroxyethylindol-5-yl, the disclosure of which is incorporated herein by reference.

The tricyclic compounds (I) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/04680, WO93/5059, etc.], the disclosures of which are incorporated herein by reference.

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Oct. 5, 1984, accession number FERM BP-927] or *Streptomyces hygroscopius* subsp. *yakushimaensis* No. 7238 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Jan. 12, 1985, accession number FERM BP-928] [EP-A-0184162]. The FK506 (general name: tacrolimus) of the following chemical formula, in particular, is a representative compound.

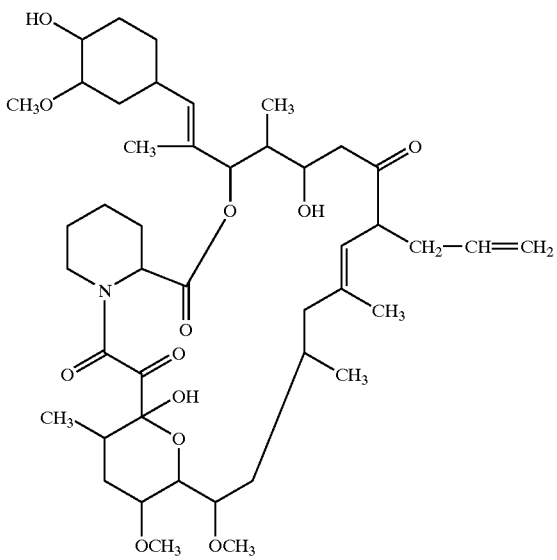

Chemical Name: 17-allyl-1,14-dihydroxy-12-[2-(4-hydroxy-3-methoxycyclohexyl) -1-methylvinyl]-23, 25-dimethoxy -13,19,21,27-tetramethyl-11, 28-dioxa-4-azatricyclo [22.3.1.0$^{4,9}$]octacos-18-ene-2,3, 10,16-tetraone The preferred examples of the tricyclic compounds (I) are the ones, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

$R^{24}$ is a 3-$R^{20}$-4-$R^{21}$-cyclohexyl group, in which $R^{20}$ is hydroxy, an alkoxy group, an oxo group, or a —OCH$_2$OCH$_2$CH$_2$OCH$_3$ group, and $R^{21}$ is hydroxy, —OCN, an alkoxy group, a heteroaryloxy which may be substituted by suitable substituents, 1- or 2-tetrazolyl, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—, in which $R^{25}$ is optionally protected hydroxy or protected amino, and $R^{26}$ is hydrogen or methyl, or $R^{20}$ and $R^{21}$ together form an oxygen atom in an epoxide ring; and n is an integer of 1 or 2.

The most preferable tricyclic compounds(I) is, in addition to FK506, ascomycin derivatives such as halogenated-ascomycin (e.g., 33-epi-chloro-33-desoxyascomycin), which is disclosed in EP 427,680, example 66a.

The tricyclic compounds(I) has a similar basic structure, i.e., tricyclic macrolide structure, and at least one of the similar biological properties (for example, immunosupressive activity).

The tricyclic compounds(I) may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the macrolide compound used in the present invention, it is to be understood that there may be conformers and one or more stereoisomers such as optical and geometrical isomers due to asymmetric carbon atom(s) or double bond(s), and such conformers and isomers are also included within the scope of macrolide compound in the present invention. And further, the macrolide compounds can be in the form of a solvate, which is included within the scope of the present invention. The solvate preferably include a hydrate and an ethanolate.

The macrolide compounds usable in the present invention may be administered as pure compounds or mixtures of compounds or preferably, in a pharmaceutical vehicle or carrier.

The pharmaceutical compositions of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external(topical), enteral, intravenous, intramuscular, or parenteral applications. The active ingredient may be compounded, for example, with the usual non-toxic, pharmaceutically acceptable, carriers for tablets, pellets, capsules, eye drops, suppositories, solutions (saline, for example), emulsion, suspensions (olive oil, for example), ointment and any other form suitable for use. The carriers which can be used are water, glucose, lactose, gum acacia, gelatin, mannitol, starch paste, magnesiumtrisilicate, talc, cornstarch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an effective amount sufficient to produce the desired effect upon the process or condition of the disease.

Mammals which may be treated using the method of the present invention include livestock mammals such as cows, horses, etc., domestic animals such as dogs, cats, rats, etc. and humans.

While the dosage of therapeutically effective amount of the macrolide compounds varies from and also depends upon the age and condition of each individual patient to be treated, a daily dose of about 0.0001–1000 mg, preferably, 0.001–500 mg and more preferably, 0.01–100 mg of the active ingredient is generally given for treating diseases, and an average single dose of about 0.001–0.01 mg, 0.2–0.5 mg, 1 mg, 5 mg, 10 mg, 50 mg, 100 mg, 250 mg and 500 mg is generally administered. Daily doses for chronic administration in humans will be in the range of about 0.1–0.3 mg/kg/day.

The following examples illustrate the present invention in further detail, it being to be understood that those examples are not intended to limit the scope of the invention.

EXAMPLE 1

| FK 506 Substance | 1 g |
| --- | --- |
| Hydroxypropyl methylcellulose 2910 (TC-5R) | 1 g |
| Lactose | 2 g |
| Croscarmellose sodium (Ac-Di-Sol) | 1 g |

The FK 506 Substance (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, maker: Asahi Chemical Industry) were homogeneously suspended to this solution, and then the organic solvent was removed by evaporation. The residual product was dried under reduced pressure for 10 hours by vacuum dryer, milled for 2 minutes by coffee mill and then passed through a sieve (32 mesh) to give the solid dispersion composition of FK 506 Substance (5 g). This composition was capsulated by a conventional manner to provide capsules containing 1 mg or 5 mg of FK 506 Substance per each capsule.

EXAMPLE 2

| FK506 Substance | 10 mg |
| --- | --- |
| HCO-60 (polyoxyethylenehydrogenated castor oil 60) | 400 mg |
| Ethanol | to 1 ml |

The solution comprising the ingredients stated above is prepared by dissolving the FK506 Substance and HCO-60 in ethanol by a conventional manner. It can be administered via intravenous infusion by diluting with a proper volume of physiological saline.

EXAMPLE 3

The inducing activity by FK506 Substance on chondrogenic differentiation was evaluated in accordance with the below-mentioned method.
(1) The ATDC5 cell line provided by RIKEN Cell Bank (Tsukuba, Japan) was grown in a 1:1 mixture of Dulbecco's modified Eagle's medium and Ham's F12 medium (Nikken Biomedical Laboratory, Kyoto, Japan) supplemented with 10 % heat-inactivated fetal bovine serum (Intergen, Purchase, N.Y.). Under these conditions, ATDC5 cells remain chondroprogenitor-like and do not express cartilage phenotypes.
(2) The above ATDC5 cells were plated in 12-multiwell plastic plate at a density of $1 \times 10^5$ cells/well in the medium. After 4 hr, the medium was replaced with fresh medium containing FK506 or Cyclosporin A (CsA), and the culture was continued for a 24 days with medium change every 2 or 3 days. Cells were fixed with methanol and stained 0.1% Alcian blue (Sigma Chemical Co., St. Louis, Mo.) dissolved in 0.1 M hydrochloric acid for 16 hr at room temperature. Cells were then rinsed three times with distilled water, and the amount of cell-associated dye was measured at 620 nm after extraction with 6 M guanidine-HCl (300 μl/well).
Results
ATDC5 cells were incubated with FK506 or CsA for 24 days and the amount of proteoglycan was assayed. The result is shown in FIG. 1.

FK506 induced differentiation into chondrocyte in a concentration-dependent manner (1–1000 ng/ml). On the other hand, CsA did not induce the differentiation.

The above results indicate that the macrolide compounds, such as FK506 Substance, are useful for preventing or treating damages of cartilage (e.g., hyaline cartilage, fibrocartilage, elastic cartilage) which are caused by external injury, inflammatory diseases, autoimmune diseases, and so on.

More particularly, the present agent is useful for preventing or treating failure of chondrocyte, such as chondrodystrophy, arthritis (e.g., rheumatoid arthritis, osteoarthritis, etc); osteoporosis; and so on.

And further, the macrolides of the present invention are also useful for regeneration of tissues, such as connective tissue (e.g., cartilaginous tissue) and/or bone tissue.

The patents, patent applications and publications cited herein are incorporated by reference.

BRIEF DESCRIPTION OF THE DRAWINGS

FIG. 1 shows the effect of FK506 and Cyclosporin A on chondrogenic differentiation of ATDC5 cells.

What is claimed is:
1. A method for inducing chondrogenic differentiation, which comprises administering a tricyclic compound of the following formula (I):

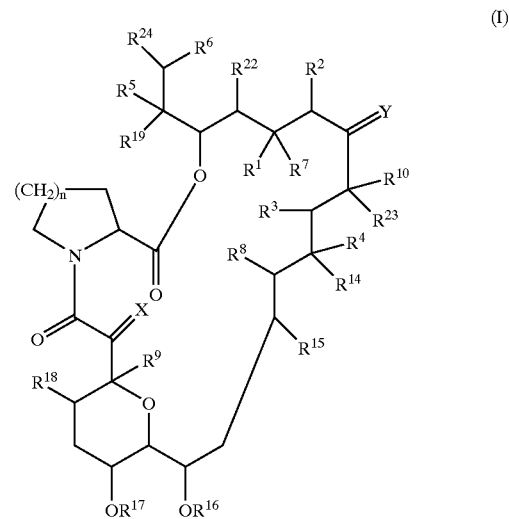

wherein each of adjacent pairs of $R^1$ and $R^2$, $R^3$ and $R^4$, and $R^5$ and $R^6$ independently
(a) are two adjacent hydrogen atoms, and $R^2$ may optionally be an alkyl group, or
(b) forms a bond between the carbon atoms to which they are attached;
$R^7$ is a hydrogen atom, a hydroxy group, a protected hydroxy group, or an alkoxy group, or an oxo group together with $R^1$;
$R^8$ and $R^9$ are independently a hydrogen atom or a hydroxy group;
$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;
X is an oxo group, a hydrogen atom and a hydroxy group, a hydrogen atom and a hydrogen atom, or X can combine with an adjacent carbonyl group to form a group of the formula —CH$_2$O—;

Y is an oxo group, a hydrogen atom and a hydroxy group, a hydrogen atom and a hydrogen atom, or a group represented by the formula N—NR$^{11}$R$^{12}$ or N—OR$^{13}$; R$^{11}$ and R$^{12}$ are independently a hydrogen atom, an alkyl group, an aryl group or a tosyl group;

R$^{13}$, R$^{14}$, R$^{15}$, R$^{16}$, R$^{17}$, R$^{18}$, R$^{19}$, R$^{22}$ and R$^{23}$ are independently a hydrogen atom or an alkyl group;

R$^{24}$ is a 3-R$^{20}$-4-R$^{21}$-cyclohexyl group, in which
R$^{20}$ is hydroxy, alkoxy, oxo or —OCH$_2$OCH$_2$CH$_2$OCH$_3$, and R$^{21}$ is hydroxy, —OCN, alkoxy, heteroaryloxy which is optionally substituted by 1- or 2-tetrazolyl, —OCH$_2$OCH$_2$CH$_2$OCH$_3$, protected hydroxy, chloro, bromo, iodo, aminooxalyloxy, azido, p-tolyloxythiocarbonyloxy or R$^{25}$R$^{26}$CHCOO—,
in which R$^{25}$ is optionally protected hydroxy or protected amino, and R$^{26}$ is hydrogen or methyl, or R$^{20}$ and R$^{21}$ together form an oxygen atom in an epoxide ring;

n is an integer of 1 or 2; and

Y, R$^{10}$ and R$^{23}$, together with the carbon atoms to which they are attached, may represent a saturated or unsaturated 5- or 6-membered heterocyclic ring containing nitrogen, sulfur, oxygen or a combination thereof, optionally substituted by one or more groups selected from the group consisting of an alkyl group, a hydroxy group, an alkoxy group, a benzyl group, a group of the formula —CH$_2$Se(C$_6$H$_5$), and an alkyl group substituted by one or more hydroxy groups; or a pharmaceutically acceptable salt thereof, to a mammal.

2. The method of claim 1, wherein the tricyclic compound is FK 506 Substance or its hydrate.

3. The method of claim 1, wherein damage to cartilage or chondrocyte dysfunction of chondrocyte is treated.

4. The method of claim 3, wherein the chondrocyte dysfunction is selected from the group consisting of chondrodystrophy, arthritis and osteoporosis.

5. The method of claim 1, wherein inducing chondrogenic differentiation regenerates connective tissue, bone tissue or a combination thereof.

6. The method of claim 5, wherein the connective tissue is cartilaginous tissue.

7. The method of claim 1, wherein the tricyclic compound is administered to a human at a daily dosage of about 0.0001 to 1000 mg.

8. The method of claim 1, wherein the tricyclic compound is administered to a human at a daily dosage of about 0.01 to 100 mg.

9. The method of claim 1, wherein the tricyclic compound is administered at an average single dose of about 0.001 to 0.01 mg.

10. The method of claim 1, comprising administering an average single dose of the tricyclic compound of 0.2 to 0.5 mg.

11. The method of claim 1, wherein the tricyclic compound is administered at an average single dose administered of 1 mg.

12. The method of claim 1, wherein the tricyclic compound is administered at an average single dose of 5 mg.

13. The method of claim 1, wherein the tricyclic compound is administered at an average single dose of 10 mg.

14. The method of claim 1, wherein the tricyclic compound is administered at an average single dose of 50 mg.

15. The method of claim 1, wherein the tricyclic compound is administered at an average single dose of 100 mg.

16. The method of claim 1, wherein the tricyclic compound is administered at an average single dose of 250 mg.

17. The method of claim 1, wherein the tricyclic compound is administered at an average single dose of 500 mg.

18. The method of claim 1, wherein the tricyclic compound is administered at a daily dose for chronic administration in humans in the range of about 0.1 to 0.3 mg/kg/day.

* * * * *